US007897615B2

(12) United States Patent
Kafka et al.

(10) Patent No.: US 7,897,615 B2
(45) Date of Patent: *Mar. 1, 2011

(54) CYANOAMIDE COMPOUNDS USEFUL AS MALONYL-COA DECARBOXYLASE INHIBITORS

(75) Inventors: Mark D. Kafka, San Diego, CA (US); Mark E. Wilson, Ramona, CA (US); Anna Russell, Ramona, CA (US); Gary D. Lopaschuk, Edmonton (CA); Jason R. Dyck, Sherwood Park (CA)

(73) Assignee: Chugai Sciyaku Kabushiki Kaisha, Tokyo (JP)

( * ) Notice: Subject to any disclaimer, the term of this patent is extended or adjusted under 35 U.S.C. 154(b) by 390 days.

This patent is subject to a terminal disclaimer.

(21) Appl. No.: 11/866,266

(22) Filed: Oct. 2, 2007

(65) Prior Publication Data

US 2008/0161358 A1 Jul. 3, 2008

Related U.S. Application Data

(63) Continuation of application No. 10/900,957, filed on Jul. 28, 2004, now Pat. No. 7,285,562.

(60) Provisional application No. 60/492,100, filed on Aug. 1, 2003.

(51) Int. Cl.
*A61K 31/44* (2006.01)
*A61K 31/41* (2006.01)
*A61K 31/425* (2006.01)
*A61K 31/42* (2006.01)

(52) U.S. Cl. ......... 514/301; 514/302; 514/361; 514/367; 514/376

(58) Field of Classification Search .................. 514/301, 514/302, 361, 367, 376
See application file for complete search history.

(56) References Cited

U.S. PATENT DOCUMENTS

| | | | |
|---|---|---|---|
| 3,728,455 A | 4/1973 | Kupfer et al. | |
| 5,177,097 A | 1/1993 | Poss | |
| 5,190,942 A | 3/1993 | Poss | |
| 5,208,234 A | 5/1993 | Poss | |
| 5,208,235 A | 5/1993 | Poss | |
| 5,212,177 A | 5/1993 | Poss | |
| 5,225,408 A | 7/1993 | Weller | |
| 5,256,695 A | 10/1993 | Poss | |
| 5,374,615 A | 12/1994 | Poss | |
| 5,378,704 A | 1/1995 | Weller | |
| 5,428,033 A | 6/1995 | Belley | |
| 5,470,975 A | 11/1995 | Atwal | |
| 5,512,681 A | 4/1996 | Boswell | |
| 5,519,143 A | 5/1996 | Harris | |
| 5,534,347 A | 7/1996 | Chen | |
| 5,736,297 A | 4/1998 | Roeschert | |
| 5,895,771 A | 4/1999 | Epstein | |
| 5,977,413 A | 11/1999 | Tomaru | |
| 7,285,562 B2 * | 10/2007 | Kafka et al. | 514/301 |

FOREIGN PATENT DOCUMENTS

| | | |
|---|---|---|
| DE | 197 16 231 A1 | 10/1998 |
| DE | 197 22 952 A1 | 10/1998 |
| EP | 0 144 101 A2 | 6/1985 |
| EP | 0 296 722 A1 | 10/1988 |
| EP | 0 481 448 A1 | 4/1992 |
| EP | 0 547 442 A1 | 6/1993 |
| EP | 0 556 060 A1 | 8/1993 |
| EP | 0 733 366 A2 | 9/1996 |
| EP | 0 733 614 A1 | 5/1998 |
| EP | 0 916 352 A2 | 12/1998 |
| FR | 2 784 114 A1 | 4/2000 |
| GB | 2 321 244 A | 7/1998 |
| GB | 2 337 701 A | 1/1999 |
| JP | 05 124925 A | 9/1993 |
| JP | 08 311036 | 11/1996 |
| JP | 09 012585 | 1/1997 |
| RU | 1743153 | 2/1995 |
| SU | 1825496 A3 | 12/1994 |
| WO | WO 87/05297 | 9/1987 |
| WO | WO 91/00277 | 1/1991 |
| WO | WO 91/00281 | 1/1991 |
| WO | WO 92/00067 | 1/1992 |
| WO | WO 93/21158 | 10/1993 |
| WO | WO 93/21168 | 10/1993 |
| WO | WO 94/10692 | 5/1994 |
| WO | WO 94/14453 | 7/1994 |

(Continued)

OTHER PUBLICATIONS

Deems et al., The American Physiological Society, 1998, R524-R528, vol. 274.
Dyck et al., The American Physiological Society, 1998, H2122-2129, vol. 275.
FitzPatrick et al., Am. J. Hum. Genet. 1999, 318-326, vol. 65.
Fraser et al., Febs Letters, 1999, 69-74, vol. 446.
Gao et al., Journal Lipid Research, 1999, 178-182, vol. 40.
Hearse, Metabolic Approaches to Ischaemic Heart Disease and it Management, Science Press, London, UK.

(Continued)

*Primary Examiner* — Raymond J Henley, III
(74) *Attorney, Agent, or Firm* — Fish & Richardson P.C.

(57) ABSTRACT

The present invention provides previous methods for the use of compounds as depicted by structure I, pharmaceutical compositions containing the same, and methods for the prophylaxis, management and treatment of metabolic diseases and diseases modulated by MCD inhibition. The compounds disclosed in this invention are useful for the prophylaxis, management and treatment of diseases involving in malonyl-CoA regulated glucose/fatty acid metabolism pathway. In particular, these compounds and pharmaceutical composition containing the same are indicated in the prophylaxis, management and treatment of cardiovascular diseases, diabetes, cancer and obesity.

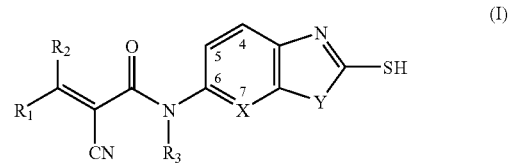

(I)

4 Claims, No Drawings

FOREIGN PATENT DOCUMENTS

| | | |
|---|---|---|
| WO | WO 94/15932 | 7/1994 |
| WO | WO 94/18606 | 8/1994 |
| WO | WO 95/35312 | 10/1995 |
| WO | WO 95/29904 A | 11/1995 |
| WO | WO 95/35311 | 12/1995 |
| WO | WO 95/35313 | 12/1995 |
| WO | WO 96/13491 | 5/1996 |
| WO | WO 96/13500 | 5/1996 |
| WO | WO 98/25931 A | 6/1998 |
| WO | WO 99/12938 | 3/1999 |
| WO | WO 99/47497 | 9/1999 |
| WO | WO 99/65884 | 12/1999 |
| WO | WO 00/09710 A | 2/2000 |
| WO | WO 00/20472 | 4/2000 |
| WO | WO 00/34344 | 6/2000 |
| WO | WO 00/37422 | 6/2000 |
| WO | WO 00/46203 | 8/2000 |
| WO | WO 00/54759 | 9/2000 |
| WO | WO 00/56710 | 9/2000 |
| WO | WO 00/69810 A | 11/2000 |
| WO | WO 01/03705 A1 | 1/2001 |
| WO | WO 02/058690 A2 | 8/2002 |
| WO | WO 02/058698 A2 | 8/2002 |
| WO | WO 02/064136 A2 | 8/2002 |

OTHER PUBLICATIONS

Jang et al., The Journal of Biological Chemistry, 1989, 3500-3505, vol. 264, No. 6.
Kantor et al., Circulation Research, 2008, 580-588, vol. 86.
Kennedy et al., Biochemical Pharmacology, 1996, 273-280, vol. 52.
Kim and Kolattukudy, Archives of Biochemistry and Biophysics, 1978, 585-597, vol. 190, No. 2.
Kim and Kolattukudy, Archives of Biochemistry and Biophysics, 1978, 234-246, vol. 190, No. 1.
Kim and Kolattukudy, Biochemica et Biophysica Acta, 1978, 187-196, vol. 531.
Loftus et al., Science, 2000, 237-238, vol. 288.
McCormack et al., Genet. Pharmac., 1998, 639-645, vol. 30, No. 5).
McGarry and Brown, Eur. J. Biochem., 1997, 1-14, vol. 244.
McNeill, Measurement of Cardiovascular Func., CRC Press, Boca Raton, USA.
Pepine et al., The American Journal of Cardiology, 1999, 46-50, vol. 84.
Pizer et al., Cancer Research, 2000, 213-218, vol. 60.
Prentki et al., Diabetes, 1996, 273-283, vol. 45.
Randle et al., Lancet, 1963, 785-789, vol. 1.
Sacksteder et al., The Journal of Biological Chemistry, 1999, 24461-24468, vol. 274, No. 35.
Voilley et al., Biochem. J., 1999, 213-217, vol. 340.
Wargovich et al., Am J Cardiol, 1988, 65-70, vol. 61.
Zammit, Biochemical Society, 1999, 505-515, vol. 343.
Database Biosis 'Online!, Biosciences Information Service, 1976, Database accession No. PREV197763044218, 002207355.
Chemical Abstracts, 1969, vol. 71, No. 23, Columbus, OH, US, XP002207359.
"Fluka Chemika-Biochemika" Fluka Chemie AG, Buchs (CH), XP002230053, 1995, 331.
Abo-Hashema et al., Biochemistry, 1999, 15840-15847, vol. 38.
Abo-Hashema et al., Journal of Biological Chemistry, 1999, 35577-35582, vol. 274, No. 50.
Alam and Saggerson, "Malonyl-CoA and the regulation of fatty acid oxidation in soleus muscle" Biochem J. 334:233-241 (1998).
An et al., Journal of Biochemistry and Molecular Biology, 1999, 414-418, vol. 32, No. 4.
Anderson, Current Pharmaceutical Design, 1998, 1-16, vol. 4, No. 1.
Buckner, et al., Archives of Biochemistry Biophysics, 1976, 539-551, vol. 177.
Cecil, Textbook of Medicine, 21$^{st}$ ed., vol. 1, published 2000 by W.B. Saunders Company (PA), pp. 1060-1074.

* cited by examiner

CYANOAMIDE COMPOUNDS USEFUL AS MALONYL-COA DECARBOXYLASE INHIBITORS

This application is a continuation and claims the benefit of priority under 35 U.S.C. Section 120 of U.S. application Ser. No. 10/900,957, filed Jul. 28, 2004 (now U.S. Pat. No. 7,285,562), which claims priority to U.S. Provisional Application No. 60/492,100, filed on Aug. 1, 2003. The disclosure of each prior application is considered part of and is incorporated by reference in the disclosure of this application.

FIELD OF THE INVENTION

The present invention relates to methods of treatment of certain metabolic diseases and the use of compounds and their prodrugs, and/or pharmaceutically acceptable salts, pharmaceutical compositions containing such compounds useful in treating such diseases. In particular, the invention relates to the use of compounds and compositions for the prophylaxis, management or treatment of cardiovascular diseases, diabetes, cancers, and obesity through the inhibition of malonyl-coenzyme A decarboxylase (malonyl-CoA decarboxylase, MCD).

BACKGROUND OF THE INVENTION

Malonyl-CoA is an important metabolic intermediary produced by the enzyme Acetyl-CoA Carboxylase (ACC) in the body. In the liver, adipocytes, and other tissues, malonyl-CoA is a substrate for fatty acid synthase (FAS). ACC and malonyl-CoA are found in skeletal muscle and cardiac muscle tissue, where fatty acid synthase levels are low. The enzyme malonyl-CoA decarboxylase (MCD, EC 4.1.1.9) catalyzes the conversion of malonyl-CoA to acetyl-CoA and thereby regulates malonyl-CoA levels. MCD activity has been described in a wide array of organisms, including prokaryotes, birds, and mammals. It has been purified from the bacteria *Rhizobium trifolii* (An et al., *J. Biochem. Mol. Biol.* 32:414-418 (1999)), the uropygial glands of waterfowl (Buckner, et al., *Arch. Biochem. Biophys* 177:539 (1976); Kim and Kolattukudy *Arch. Biochem. Biophys* 190:585 (1978)), rat liver mitochondria (Kim and Kolattukudy, *Arch. Biochem. Biophys.* 190:234 (1978)), rat mammary glands (Kim and Kolattukudy, *Biochim. Biophys, Acta* 531:187 (1978)), rat pancreatic β-cell (Voilley et al., *Biochem. J.* 340:213 (1999)) and goose (*Anser anser*) (Jang et al., *J. Biol. Chem.* 264:3500 (1989)). Identification of patients with MCD deficiency lead to the cloning of a human gene homologous to goose and rat MCD genes (Gao et al., *J. Lipid. Res.* 40:178 (1999); Sacksteder et al., *J. Biol. Chem.* 274:24461 (1999); FitzPatrick et al., *Am. J. Hum. Genet.* 65:318 (1999)). A single human MCD mRNA is observed by Northern Blot analysis. The highest mRNA expression levels are found in muscle and heart tissues, followed by liver, kidney and pancreas, with detectable amounts in all other tissues examined.

Malonyl-CoA is a potent endogenous inhibitor of carnitine palmitoyltransferase-I (CPT-I), an enzyme essential for the metabolism of long-chain fatty acids. CPT-I is the rate-limiting enzyme in fatty acid oxidation and catalyzes the formation of acyl-carnitine, which is transported from the cytosol across the mitochondrial membranes by acyl carnitine translocase. Inside of the mitochondria the long-chain fatty acids are transferred back to CoA form by a complementary enzyme, CPT-II, and, in the mitochondria, acyl-CoA enters the β-oxidation pathway generating acetyl-CoA. In the liver, high levels of acetyl-CoA occurs for example following a meal, leading to elevated malonyl-CoA levels, which inhibit CPT-I, thereby preventing fat metabolism and favoring fat synthesis. Conversely, low malonyl-CoA levels favor fatty acid metabolism by allowing the transport of long-chain fatty acids into the mitochondria. Hence, malonyl-CoA is a central metabolite that plays a key role in balancing fatty acid synthesis and fatty acid oxidation (Zammit, *Biochem. J.* 343: 5050-515 (1999)). Recent work indicates that MCD is able to regulate cytoplasmic as well as mitochondrial malonyl-CoA levels [Alam and Saggerson, *Biochem J.* 334:233-241 (1998); Dyck et al., *Am J Physiology* 275:H2122-2129 (1998)].

Although malonyl-CoA is present in muscle and cardiac tissues, only low levels of FAS have been detected in these tissues. It is believed that the role of malonyl-CoA and MCD in these tissues is to regulate fatty acid metabolism. This is achieved via malonyl-CoA inhibition of muscle (M) and liver (L) isoforms of CPT-I, which are encoded by distinct genes (McGarry and Brown, *Eur. J. Biochem.* 244:1-14 (1997)). The muscle isoform is more sensitive to malonyl-CoA inhibition ($IC_{50}$ 0.03 μM) than the liver isoform ($IC_{50}$ 2.5 μM). Malonyl-CoA regulation of CPT-I has been described in the liver, heart, skeletal muscle and pancreatic β-cells. In addition, malonyl-CoA sensitive acyl-CoA transferase activity present in microsomes, perhaps part of a system that delivers acyl groups into the endoplasmic reticulum, has also been described (Fraser et al., *FEBS Lett.* 446: 69-74 (1999)).

Cardiovascular Diseases: The healthy human heart utilizes available metabolic substrates. When blood glucose levels are high, uptake and metabolism of glucose provide the major source of fuel for the heart. In the fasting state, lipids are provided by adipose tissues, and fatty acid uptake and metabolism in the heart down regulate glucose metabolism. The regulation of intermediary metabolism by serum levels of fatty acid and glucose comprises the glucose-fatty acid cycle (Randle et al., *Lancet*, 1:785-789 (1963)). Under ischemic conditions, limited oxygen supply reduces both fatty acid and glucose oxidation and reduces the amount of ATP produced by oxidative phosphorylation in the cardiac tissues. In the absence of sufficient oxygen, glycolysis increases in an attempt to maintain ATP levels and a buildup of lactate and a drop in intracellular pH results. Energy is spent maintaining ion homeostasis, and myocyte cell death occurs as a result of abnormally low ATP levels and disrupted cellular osmolarity. Additionally, AMPK, activated during ischemia, phosphorylates and thus inactivates ACC. Total cardiac malonyl-CoA levels drop, CPT-I activity therefore is increased and fatty acid oxidation is favored over glucose oxidation. The beneficial effects of metabolic modulators in cardiac tissue are the increased efficiency of ATP/mole oxygen for glucose as compared to fatty acids and more importantly the increased coupling of glycolysis to glucose oxidation resulting in the net reduction of the proton burden in the ischemic tissue.

A number of clinical and experimental studies indicate that shifting energy metabolism in the heart towards glucose oxidation is an effective approach to decreasing the symptoms associated with cardiovascular diseases, such as but not limited, to myocardial ischemia (Hearse, "*Metabolic approaches to ischemic heart disease and its management*", Science Press). Several clinically proven anti-angina drugs including perhexyline and amiodarone inhibit fatty acid oxidation via inhibition of CPT-I (Kennedy et al., *Biochem. Pharmacology*, 52: 273 (1996)). The antianginal drugs ranolazine, currently in Phase III clinical trials, and trimetazidine are shown to inhibit fatty acid β-oxidation (McCormack et al., *Genet. Pharmac.* 30:639 (1998), Pepine et al., *Am. J. Cardiology* 84:46 (1999)). Trimetazidine has been shown to specifically inhibit the long-chain 3-ketoactyl CoA thiolase, an essential step in fatty acid oxidation. (Kantor et al., *Circ. Res.* 86:580-588 (2000)). Dichloroacetate increases glucose oxidation by stimulating the pyruvate dehydrogenase complex and improves cardiac function in those patients with coronary artery diseases (Wargovich et al., *Am. J. Cardiol.* 61:65-70 (1996)). Inhibiting CPT-I activity through the increased malonyl-CoA levels with MCD inhibitors would result in not only a novel, but also a much safer method, as compared to other known small molecule CPT-I inhibitors, to the prophylaxis and treatment of cardiovascular diseases.

Most of the steps involved in glycerol-lipid synthesis occur on the cytosolic side of liver endoplasmic reticulum (ER) membrane. The synthesis of triacyl glycerol (TAG) targeted for secretion inside the ER from diacyl glycerol (DAG) and acyl CoA is dependent upon acyl CoA transport across the ER membrane. This transport is dependent upon a malonyl-CoA sensitive acyl-CoA transferase activity (Zammit, *Biochem. J.* 343: 505 (1999) Abo-Hashema, *Biochem.* 38: 15840 (1999) and Abo-Hashema, *J. Biol. Chem.* 274:35577 (1999)). Inhibition of TAG biosynthesis by a MCD inhibitor may improve the blood lipid profile and therefore reduce the risk factor for coronary artery disease of patients.

Diabetes: Two metabolic complications most commonly associated with diabetes are hepatic overproduction of ketone bodies (in NIDDM) and organ toxicity associated with sustained elevated levels of glucose. Inhibition of fatty acid oxidation can regulate blood-glucose levels and ameliorate some symptoms of type II diabetes. Malonyl-CoA inhibition of CPT-I is the most important regulatory mechanism that controls the rate of fatty acid oxidation during the onset of the hypoinsulinemic-hyperglucagonemic state. Several irreversible and reversible CPT-I inhibitors have been evaluated for their ability to control blood glucose levels and they are all invariably hypoglycemic (Anderson, *Current Pharmaceutical Design* 4:1 (1998)). A liver specific and reversible CPT-inhibitor, SDZ-CPI-975, significantly lowers glucose levels in normal 18-hour-fasted nonhuman primates and rats without inducing cardiac hypertrophy (Deems et al., *Am. J. Physiology* 274:R524 (1998)). Malonyl-CoA plays a significant role as a sensor of the relative availability of glucose and fatty acid in pancreatic β-cells, and thus links glucose metabolism to cellular energy status and insulin secretion. It has been shown that insulin secretagogues elevate malonyl-CoA concentration in β-cells (Prentki et al., *Diabetes* 45: 273 (1996)). Treating diabetes directly with CPT-I inhibitors has, however, resulted in mechanism-based hepatic and myocardial toxicities. MCD inhibitors that inhibit CPT-I through the increase of its endogenous inhibitor, malonyl-CoA, are thus safer and superior as compared to CPT-I inhibitors for treatment of diabetic diseases.

Cancers: Malonyl-CoA has been suggested to be a potential mediator of cytotoxicity induced by fatty-acid synthase inhibition in human breast cancer cells and xenografts (Pizer et al., *Cancer Res.* 60:213 (2000)). It is found that inhibition of fatty acid synthase using antitumor antibiotic cerulenin or a synthetic analog C75 markedly increase the malonyl-CoA levels in breast carcinoma cells. On the other hand, the fatty acid synthesis inhibitor, TOFA (5-(tetradecyloxy)-2-furoic acid), which only inhibits at the acetyl-CoA carboxylase (ACC) level, does not show any antitumor activity, while at the same time the malonyl-CoA level is decreased to 60% of the control. It is believed that the increased malonyl-CoA level is responsible for the antitumor activity of these fatty acid synthase inhibitors. Regulating malonyl-CoA levels using MCD inhibitors thus constitutes a valuable therapeutic strategy for the treatment of cancer diseases.

Obesity: It is suggested that malonyl-CoA may play a key role in appetite signaling in the brain via the inhibition of the neuropeptide Y pathway (Loftus et al., *Science* 288: 2379 (2000)). Systemic or intracerebroventricular treatment of mice with fatty acid synthase (FAS) inhibitor cerulenin or C75 led to inhibition of feeding and dramatic weight loss. It is found that C75 inhibited expression of the prophagic signal neuropeptide Y in the hypothalamus and acted in a leptin-independent manner that appears to be mediated by malonyl-CoA. Therefore control of malonyl-CoA levels through inhibition of MCD provides a novel approach to the prophylaxis and treatment of obesity.

We have now found a novel use for compounds containing thiazoles and oxazoles, members of which are potent inhibitors of MCD. The compounds tested both in vitro and in vivo inhibit malonyl-CoA decarboxylase activities and increase the malonyl-CoA concentration in the animal tissues. In addition, by way of example, selected compounds induce a significant increase in glucose oxidation as compared with the control in an isolated perfused rat heart assay (McNeill, *Measurement of Cardiovascular Function*, CRC Press, 1997). Advantageously, preferred compounds embodied in this application have more profound effects in metabolism shift than the known metabolism modulators such as ranolazine or trimetazidine. The compounds useful for this invention and pharmaceutical compositions containing these compounds are therefore useful in medicine, especially in the prophylaxis, management and treatment of various cardiovascular diseases, diabetes, cancers and obesity.

Additionally, these compounds are also useful as a diagnostic tool for diseases associated with MCD deficiency or malfunctions.

SUMMARY OF THE INVENTION

The present invention provides methods for the use of compounds as depicted by structure I, pharmaceutical compositions containing the same, and methods for the prophylaxis, management and treatment of metabolic diseases and diseases modulated by MCD inhibition. The compounds disclosed in this invention are useful for the prophylaxis, management and treatment of diseases involving in malonyl-CoA regulated glucose/fatty acid metabolism pathway. In particular, these compounds and pharmaceutical composition containing the same are indicated in the prophylaxis, management and treatment of cardiovascular diseases, diabetes, cancer and obesity.

The present invention also includes within its scope diagnostic methods for the detection of diseases associated with MCD deficiency or malfunctions.

The compounds useful in the present invention are represented by the following structure (1):

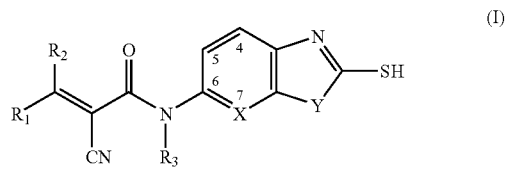

Wherein $R_1$, $R_2$, $R_3$, X and Y are as defined below. Also included within the scope of these compounds are the corresponding enantiomers, diastereoisomers, prodrugs, and pharmaceutically acceptable salts. Other aspects of this invention will become apparent as the description of this invention continues. Hence, the foregoing merely summarizes certain aspects of the invention and is not intended, nor should it be construed, as limiting the invention in any way.

DETAILED DESCRIPTION OF THE INVENTION

The detailed description of the invention that follows is not intended to be exhaustive or to limit the invention to the precise details disclosed. It has been chosen and described to best explain the details of the invention to others skilled in the art.

The compounds useful in the present invention are represented by the following formulae (I):

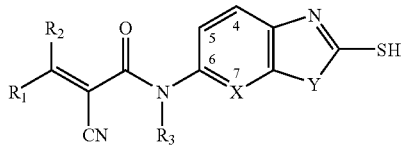

(I)

wherein $R_1$ and $R_2$ are independently selected from hydrogen, hydroxyl, alkoxyl, phenoxyl, substituted phenoxyl, substituted $C_1$-$C_{12}$ alkyl, substituted $C_1$-$C_{12}$ alkenyl, substituted $C_2$-$C_{12}$ alkynyl, phenyl, substituted phenyl, aryl, or heteroaryl, or $R_1$ and $R_2$ together form a 5 to 7 membered ring with each other;

$R_3$ is selected from hydrogen, $C_1$-$C_{12}$ alkyl, substituted $C_1$-$C_{12}$ alkyl, phenyl, substituted phenyl, aryl or heteroaryl;

X is C or N;

Y is S or O;

its corresponding enantiomers, diastereoisomers or tautomers, or a pharmaceutically acceptable salt, or a prodrug thereof in an pharmaceutically-acceptable carrier.

Preferably, the compounds in the present invention are represented by the following formula (Ia and Ib):

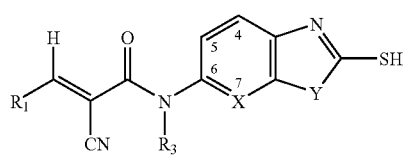

Ia

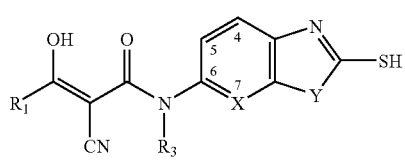

Ib wherein $R_1$, $R_3$, X and Y are as defined above.

More preferably, the compounds in the present invention are represented by the following formula (Ic and Id):

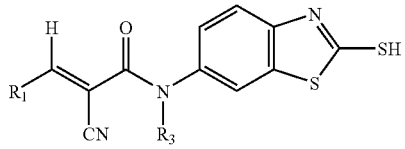

Ic

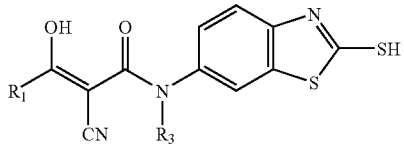

Id wherein $R_1$ and $R_3$ are as defined above.

Compositions

The compositions of the present invention comprise:
(a) a safe and therapeutically effective amount of an MCD inhibiting compound I or II, its corresponding enantiomer, diastereoisomer or tautomer, or pharmaceutically acceptable salt, or a prodrug thereof; and
(b) a pharmaceutically-acceptable carrier.

As discussed above, numerous diseases can be mediated by MCD related therapy.

Accordingly, the compounds useful in this invention can be formulated into pharmaceutical compositions for use in prophylaxis, management and treatment of these conditions. Standard pharmaceutical formulation techniques are used, such as those disclosed in Remington's Pharmaceutical Sciences, Mack Publishing Company, Easton, Pa.

A "safe and therapeutically effective amount" of a compound useful in the present invention is an amount that is effective, to inhibit MCD at the site(s) of activity, in a subject, a tissue, or a cell, and preferably in an animal, more preferably in a mammal, without undue adverse side effects (such as toxicity, irritation, or allergic response), commensurate with a reasonable benefit/risk ratio, when used in the manner of this invention. The specific "safe and therapeutically effective amount" will, obviously, vary with such factors as the particular condition being treated, the physical condition of the patient, the duration of treatment, the nature of concurrent therapy (if any), the specific dosage form to be used, the carrier employed, the solubility of the compound therein, and the dosage regimen desired for the composition.

In addition to the selected compound useful for the present invention, the compositions of the present invention contain a pharmaceutically-acceptable carrier. The term "pharmaceutically-acceptable carrier", as used herein, means one or more compatible solid or liquid filler diluents or encapsulating substances which are suitable for administration to a mammal. The term "compatible", as used herein, means that the components of the composition are capable of being comingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc;

solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4. In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a compound that is suitable for administration to an animal, preferably mammal subject, in a single dose, according to good medical practice. (The preparation of a single or unit dosage form however, does not imply that the dosage form is administered once per day or once per course of therapy. Such dosage forms are contemplated to be administered once, twice, thrice or more per day, and are expected to be given more than once during a course of therapy, though a single administration is not specifically excluded. The skilled artisan will recognize that the formulation does not specifically contemplate the entire course of therapy and such decisions are left for those skilled in the art of treatment rather than formulation.) These compositions preferably contain from about 5 mg (milligrams), more preferably from about 10 mg to about 1000 mg, more preferably to about 500 mg, most preferably to about 300 mg, of the selected compound.

The compositions useful for this invention may be in any of a variety of forms, suitable (for example) for oral, nasal, rectal, topical (including transdermal), ocular, intracerebrally, intravenous, intramuscular, or parenteral administration. (The skilled artisan will appreciate that oral and nasal compositions comprise compositions that are administered by inhalation, and made using available methodologies.) Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods of this invention are described in the following references, all incorporated by reference herein: Modern Pharmaceutics, Chapters 9 and 10 (Banker & Rhodes, editors, 1979); Lieberman et al., Pharmaceutical Dosage Forms: Tablets (1981); and Ansel, Introduction to Pharmaceutical Dosage Forms 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL R-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct application or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the compound. Suitable carriers for topical administration preferably remain in place on the skin as a continuous film, and resist being removed by perspiration or immersion in water. Generally, the carrier is organic in nature and capable of having dispersed or dissolved therein the compound. The carrier may include pharmaceutically-acceptable emollient, emulsifiers, thickening agents, solvents and the like.

Methods of Administration

The compounds and compositions useful in this invention can be administered topically or systemically. Systemic application includes any method of introducing compound into the tissues of the body, e.g., intra-articular, intrathecal, epidural, intramuscular, transdermal, intravenous, intraperitoneal, subcutaneous, sublingual administration, inhalation, rectal, or oral administration. The compounds useful in the present invention are preferably administered orally.

The specific dosage of the compound to be administered, as well as the duration of treatment is to be individualised by the treating clinicians. Typically, for a human adult (weighing approximately 70 kilograms), from about 5 mg, preferably from about 10 mg to about 3000 mg, more preferably to about 1000 mg, more preferably to about 300 mg, of the selected compound is administered per day. It is understood that these dosage ranges are by way of example only, and that daily administration can be adjusted depending on the factors listed above.

In all of the foregoing, of course, the compounds useful in the present invention can be administered alone or as mixtures, and the compositions may further include additional drugs or excipients as appropriate for the indication. For example, in the treatment of cardiovascular diseases, it is clearly contemplated that the invention may be used in conjunction with beta-blockers, calcium antagonists, ACE inhibitors, diuretics, angiotensin receptor inhibitors, or known cardiovascular drugs or therapies. Hence, in this example, compounds or compositions useful in this invention are useful when dosed together with another active and can be combined in a single dosage form or composition.

These compositions can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

DEFINITIONS

As used herein, "alkyl" means a straight chain alkane, alkene, or alkyne substituent containing only carbon and hydrogen, such as methyl, ethyl, butyl, pentyl, heptyl and the like. Alkyl groups can be saturated or unsaturated (i.e., containing —C=C— or —C≡C— linkages), at one or several positions. When a specific degree of unsaturation is preferred, said substituent is referred to as either "alkenyl" or "alkynyl", denoting substituents containing —C=C— or —C≡C— linkages, respectively. The number of carbons may be denoted as "$C_i$-$C_j$-alkyl" wherein I and j refer to the minimum and maximum number of carbon atoms, respectively. Typically, alkyl groups will comprise 1 to 12 carbon atoms, preferably 1 to 10, and more preferably 2 to 8 carbon atoms.

As used herein, "substituted alkyl" means a hydrocarbon substituent, which is linear, cyclic or branched, in which one or more hydrogen atoms are substituted by carboxy, hydroxy, alkoxy, cyano, nitro, carbonyl, aryl, carboxyalkyl, mercapto, amino, amido, ureido, carbamoyl, sulfonamido, sulfamido, or halogen. Preferred substituted alkyls have their alkyl spacers (i.e., portion which is alkyl) of 1 to about 5 carbons, and may be branched or linear, and may include cyclic substituents, either as part or all of their structure. Preferred examples of "substituted alkyls" include 4-carboxybutyl, pyridin-2-ylmethyl, and 1,3-thiazol-2-ylmethyl, benzyl, phenethyl, and trifluoromethyl. The term "substituted alkyl" may be combined with other art accepted terms. For example "substituted alkoxy" means alkoxy as understood in the art, wherein the alkyl portion of the substituent is substituted.

As used herein, "branched alkyl" means a subset of "alkyl", and thus is a hydrocarbon substituent, which is branched. Preferred branched alkyls are of 3 to about 12 carbons, and may include cycloalkyl within their structure. Examples of branched alkyl include isopropyl, isobutyl, 1,2-dimethyl-propyl, cyclopentylmethyl and the like. The term "branched alkyl" may be combined with other art accepted terms. For example "branched alkoxy" means alkoxy as understood in the art, wherein the alkyl portion of the substituent is branched.

As used herein, "cycloalkyl" is a hydrocarbon substituent that is cyclic, and can be substituted or unsubstituted. Where it is substituted, one or more hydrogen atoms are substituted by carboxy, hydroxy, alkoxy, cyano, nitro, carbonyl, aryl, carboxyalkyl, mercapto, amino, amido, ureido, carbamoyl, sulfonamido, sulfamido, or halogen. Preferred cyclic alkyls are of 3 to about 7 carbons. Examples of cycloalkyl include cyclopropyl, cyclopentyl, 4-fluoro-cyclohexyl, 2,3-dihydroxy-cyclopentyl, and the like.

As used herein, "alkylene" is an alkyl diradical, i.e., an alkyl that has open valences on two different carbon atoms. Hence "(alkylene)$R_i$" is an alkyl diradical attached at one carbon and having substituent $R_i$ attached at another carbon, which may be one or more carbons away from the point of attachment. Alkylene can be linear, branched, or cyclic. Examples of alkylene include —CH$_2$—, CH$_2$CH$_2$—, —(CH$_2$)$_4$—, -(cyclohexyl)-, and the like.

As used herein, "aryl" is a substituted or unsubstituted aromatic, i.e., Hückel 4n+2 rule applies, radical having a single-ring (e.g., phenyl) or multiple condensed rings (e.g., naphthyl or anthryl), which may contain zero to 4 heteroatoms. Hence the term "heteroaryl" is clearly contemplated in the term "aryl". Preferred carbocyclic aryl, is phenyl. Preferred monocyclic heterocycles, i.e., heteroaryls, are 5 or 6 membered rings. Preferably, where the term "aryl" represents an aromatic heterocycle, it is referred to as "heteroaryl" or "heteroaromatic", and has one or more heteroatom(s). Preferred numbers of such heteroatoms are from one to three N atoms, and preferably when "heteroaryl" is a heterocycle of five members, it has one or two heteroatoms selected from O, N, or S. Hence, preferred heterocycles have up to three, more preferably two or less, heteroatoms present in the aromatic ring. The skilled artisan will recognize that among heteroaryl, there are both five and six membered rings. Examples of "heteroaryl" include; thienyl, pyridyl, pyrimidyl, pyridazyl, furyl, oxazolyl, imidazolyl, thiazolyl, oxadiazolyl, triazinyl, triazolyl, thiadiazolyl, and others, which the skilled artisan will recognize. In this definition it is clearly contemplated that substitution on the aryl ring is within the scope of this invention. Where substitution occurs, the radical is referred to as "substituted aryl". Preferably one to three, more preferably one or two, and most preferably one substituent is attached to the aryl ring. Although many substituents will be useful, preferred substituents include those commonly found in aryl compounds, such as alkyl, hydroxy, alkoxy, cyano, nitro, halo, haloalkyl, mercapto and the like. Such substituents are prepared using known methodologies. These substituents may be attached at various positions of the aryl ring, and wherein a given placement is preferred, such placement is indicated by "o,m,p-$R_i$-aryl". Thus, if substituent $R_i$ is attached at the para position of the aryl, then this is indicated as "p-$R_i$-substituted aryl".

As used herein, "amide" includes both RNR'CO— (in the case of R=alkyl, alkaminocarbonyl-) and RCONR'— (in the case of R=alkyl, alkyl carbonylamino-).

As used herein, "ester" includes both ROCO— (in the case of R=alkyl, alkoxycarbonyl-) and RCOO— (in the case of R=alkyl, alkylcarbonyloxy-).

As used herein, "halogen" is a chloro, bromo, fluoro or iodo atom radical. Chloro, bromo and fluoro are preferred halogens. The term "halogen" also contemplates terms sometimes referred to as "halo" or "halide".

As used herein, "alkylamino" is an amine radical in which at least one hydrogen atom on the nitrogen has been replaced with alkyl. Preferred examples include ethylamino, butylamino, isopropylamino, and the like. The alkyl component may be linear, branched, cyclic, substituted, saturated, or unsaturated.

As used herein, "alkylsulfanyl" is a thiol radical in which the hydrogen atom on sulfur has been replaced with alkyl. Preferred examples include ethylsulfanyl, butylsulfanyl, isopropylsulfanyl, and the like. The alkyl component may be linear, branched, cyclic, substituted, saturated, or unsaturated.

As used herein, "alkoxy" is a hydroxyl radical in which the hydrogen atom on oxygen has been replaced with alkyl. Preferred examples include ethoxy, butoxy, benzyloxy, and the like. The alkyl component may be linear, branched, cyclic, substituted, saturated, or unsaturated.

As used herein, "heterocycle(s)" means ring systems, preferably of 3-7 members, which are saturated or unsaturated, and non-aromatic. These may be substituted or unsubstituted, and are attached to other parts of the molecule via any available valence, preferably any available carbon or nitrogen. More preferred heterocycles are of 5 or 6 members. In six-membered monocyclic heterocycles, the heteroatom(s) are from one to three of O, S, or N, and wherein when the heterocycle is five-membered, preferably it has one or two heteroatoms selected from O, N, or S.

As used herein, "heterocyclyl" means radical heterocycles. These may be substituted or unsubstituted, and are attached to other via any available valence, preferably any available carbon or nitrogen.

As used herein, "sulfamido" means an alkyl-N—S(O)$_2$N—, aryl-NS(O)$_2$N— or heterocyclyl-NS(O)$_2$N— group wherein the alkyl, aryl or heterocyclyl group is as defined herein above.

As used herein, "sulfonamido" means an alkyl-S(O)$_2$N—, aryl-S(O)$_2$N— or heterocyclyl-S(O)$_2$N— group wherein the alkyl, aryl or heterocyclyl group is as herein described.

As used herein, "ureido" means an alkyl-NCON—, aryl-NCON— or heterocyclyl-NCON— group wherein the alkyl, aryl or heterocyclyl group is as herein described.

A substituent referred to as a radical in this specification may form a ring with another radical as described herein. When such radicals are combined, the skilled artisan will understand that there are no unsatisfied valences in such a case, but that specific substitutions, for example a bond for a hydrogen, is made. Hence certain radicals can be described as forming rings together. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. Compounds described herein may have cyclic structures therein, such as a ring $R_1$ and $R_2$. In that regard the skilled artisan recognizes that this method of description is routine in medicinal chemistry, though such may not rigorously reflect the chemical synthetic route. As used herein the term "ring" or "rings" when formed by the combination of two radicals refers to heterocyclic or carbocyclic radicals, and such radicals may be saturated, unsaturated, or aromatic. For example, preferred heterocyclic ring systems include heterocyclic rings, such as morpholinyl, piperidinyl, imidazolyl, pyrrolidinyl, and pyridyl.

The skilled artisan will recognize that the radical of formula:

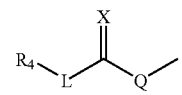

represents a number of different functionalities. Preferred functionalities represented by this structure include amides, ureas, thioureas, carbamates, esters, thioesters, amidines, ketones, oximes, nitroolefines, hydroxyguanidines and guanidines. More preferred functionalities include ureas, thioureas, amides, and carbamates.

The skilled artisan will recognize that some structures described herein may be resonance forms or tautomers of compounds that may be fairly represented by other chemical structures. The artisan recognizes that such structures are clearly contemplated within the scope of this invention, although such resonance forms or tautomers are not represented herein. For example, the structures:

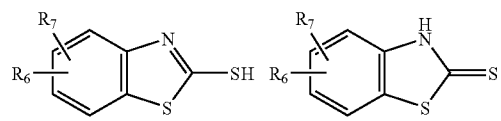

clearly represent the same compound(s), and reference to either clearly contemplates the other. In addition, the compounds useful in this invention can be provided as prodrugs, the following of which serve as examples:

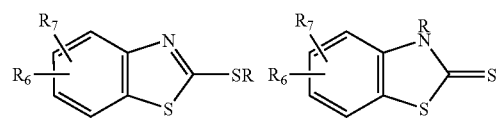

wherein R is a group (or linkage) removed by biological processes. Hence, clearly contemplated in this invention is the use compounds provided as biohydrolyzable prodrugs, as they are understood in the art. "Prodrug", as used herein is any compound wherein when it is exposed to the biological processes in an organism, is hydrolyzed, metabolized, derivatized or the like, to yield an active substance having the desired activity. The skilled artisan will recognize that prodrugs may or may not have any activity as prodrugs. It is the intent that the prodrugs described herein have no deleterious effect on the subject to be treated when dosed in safe and effective amounts. These include for example, biohydrolyzable amides and esters. A "biohydrolyzable amide" is an amide compound which does not essentially interfere with the activity of the compound, or that is readily converted in vivo by a cell, tissue, or human, mammal, or animal subject to yield an active compound. A "biohydrolyzable ester" refers to an ester compound that does not interfere with the activity of these compounds or that is readily converted by an animal to yield an active compound. Such biohydrolyzable prodrugs are understood by the skilled artisan and are embodied in regulatory guidelines.

Compounds and compositions herein also specifically contemplate pharmaceutically acceptable salts, whether cationic or anionic. A "pharmaceutically-acceptable salt" is an anionic salt formed at any acidic (e.g., carboxyl) group, or a cationic salt formed at any basic (e.g., amino) group. Many such salts are known in the art, as described in World Patent Publication 87/05297, Johnston et al., published Sep. 11, 1987 (incorporated by reference herein). Preferred counterions of salts formable at acidic groups can include cations of salts, such as the alkali metal salts (such as sodium and potassium), and alkaline earth metal salts (such as magnesium and calcium) and organic salts. Preferred salts formable at basic sites include anions such as the halides (such as chloride salts). Of course, the skilled artisan is aware that a great number and variation of salts may be used, and examples exist in the literature of either organic or inorganic salts useful in this manner.

Inasmuch as the compounds useful in this invention may contain one or more stereogenic centers, "Optical isomer", "stereoisomer", "enantiomer," "diastereomer," as referred to herein have the standard art recognized meanings (cf. *Hawleys Condensed Chemical Dictionary*, 11th Ed.) and are included in these compounds, whether as racemates, or their optical isomers, stereoisomers, enantiomers, and diastereomers.

As used herein, the term "metabolic disease", means a group of identified disorders in which errors of metabolism, imbalances in metabolism, or sub-optimal metabolism occur. The metabolic diseases as used herein also contemplate a disease that can be treated through the modulation of metabolism, although the disease itself may or may not be caused by specific metabolism blockage. Preferably, such metabolic disease involves glucose and fatty acid oxidation pathway. More preferably, such metabolic disease involves MCD or is modulated by levels of Malonyl CoA, and is referred to herein as an "MCD or MCA related disorder."

Preparation of Compounds Useful in this Invention

The starting materials used in preparing the compounds useful in this invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of these compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, reductive alkylation of amines, oxidations, acylations, aromatic substitutions, both electrophilic and nucleophilic, etherifications, esterification, saponification and the like. These manipulations are discussed in standard texts such as March Advanced Organic Chemistry (Wiley), Carey and Sundberg, *Advanced Organic Chemistry* and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis*, $2^{nd}$ Ed., John Wiley & Sons (1991).

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure.

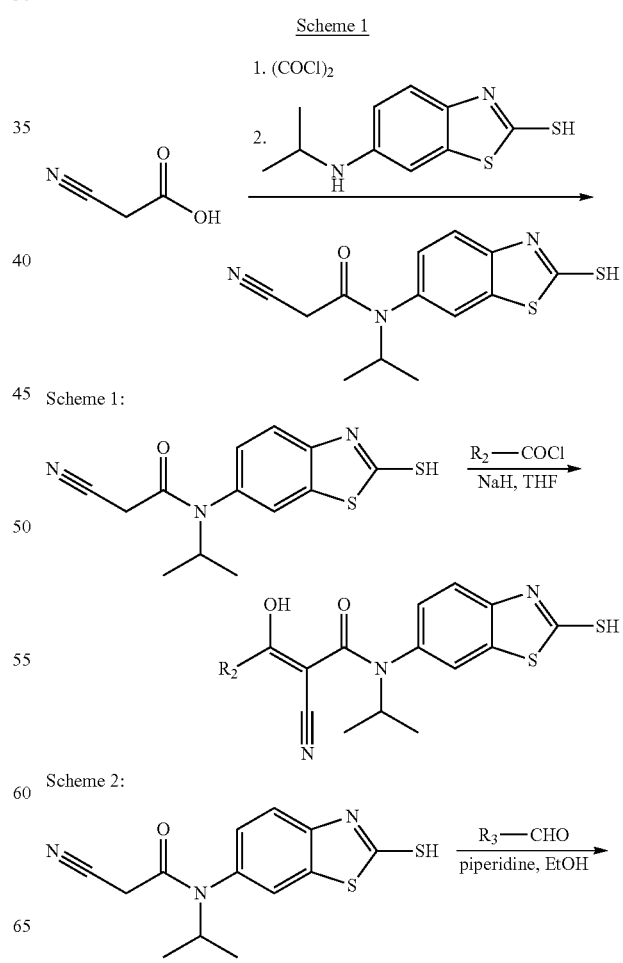

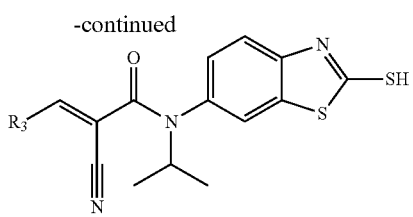

In Vitro MCD Inhibitory Assay:

The conversion of acetyl-CoA from malonyl-CoA was assayed using a modified protocol as previously described by Kim, Y. S, and Kolattukudy, P. E. in 1978 (*Arch. Biochem. Biophys* 190:585 (1978)). As shown in eq. 1-3, the establishment of the kinetic equilibrium between malate/NAD and oxaloacetate/NADH was catalyzed by malic dehydrogenase (eq. 2). The enzymatic reaction product of MCD, acetyl-CoA, shifted the equilibrium by condensing with oxaloacetate in the presence of citrate synthase (eq. 3), which resulted in a continuous generation of NADH from NAD. The accumulation of NADH can be continuously followed by monitoring the increase of fluorescence emission at 460 nm on a fluorescence plate reader. The fluorescence plate reader was calibrated using the authentic acetyl-CoA from Sigma. For a typical 96-well plate assay, the increase in the fluorescence emission ($\lambda_{ex}$=360 nm, $\lambda_{em}$=460 nm, for NADH) in each well was used to calculate the initial velocity of hMCD. Each 50 µL assay contained 10 mM phosphate buffered saline (Sigma), pH 7.4, 0.05% Tween-20, 25 mM $K_2HPO_4$—$KH_2PO_4$ (Sigma), 2 mM Malate (Sigma), 2 mM NAD (Boehringer Mannheim), 0.786 units of MD (Roche Chemicals), 0.028 unit of CS (Roche Chemicals), 5-10 nM hMCD, and varying amounts of MCA substrate. Assays were initiated by the addition of MCA, and the rates were corrected for the background rate determined in the absence of hMCD.

Isolated Working Rat Heart Assay Protocol

Isolated working hearts from male Sprague-Dawley rats (300-350 g) are subjected to a 60-minute aerobic perfusion period. The working hearts are perfused with 95% $O_2$, 5% $CO_2$ with a modified Krebs-Henseleit solution containing 5 mM glucose; 100 µU/mL insulin; 3% fatty acid-free BSA; 2.5 mM free $Ca^{2+}$, and 0.4 to 1.2 mmol/L palmitate (Kantor et al., *Circulation Research* 86:580-588 (2000)). The test compound is added 5 minutes before the perfusion period. DMSO (0.05%) is used as control.

Measurement of Glucose Oxidation Rates

Samples were taken at 10-minute intervals for measurements of experimental parameters. Glucose oxidation rates are determined by the quantitative collection of $^{14}CO_2$ produced by hearts perfused with buffer containing [U14]-Glucose (R. Barr and G. Lopaschuk, in "*Measurement of cardiovascular function*", McNeill, J. H. ed., Chapter 2, CRC press, New York (1997)). After the perfusion, the $^{14}CO_2$ from the perfusate is subsequently released by injecting 1 mL of perfusate into sealed test tube containing 1 mL of 9N $H_2SO_4$. The tube was sealed with a rubber stopper attached to a scintillation vial containing a piece of filter papers saturated with 300 µl of hyamine hydroxide. The scintillation vials with filter papers were then removed and Ecolite Scintillation Fluid added. Samples were counted by standard procedures as described above. Average rates of glucose oxidation for each phase of perfusion are expressed as µmol/min/g dry wt as described above.

Measurement of Fatty Acid Oxidation Rates:

Rates of fatty acid oxidation are determined using the same method as described above for glucose oxidation rate measurement using [$^{14}C$]palmitate or by the quantitative collection of $^3H_2O$ produced by hearts perfused with buffer containing [5-$^3H$]palmitate (R. Barr and G. Lopaschuk, in "*Measurement of cardiovascular function*", McNeill, J. H. ed., Chapter 2, CRC press, New York (1997)). $^3H_2O$ was separated from [5-$^3H$]palmitate by treating 0.5 mL buffer samples with 1.88 mL of a mixture of chloroform/methanol (1:2 v:v) and then adding 0.625 mL of chloroform and 0.625 mL of a 2 M KCl/HCl solution. The sample is centrifuged for 10 min and aqueous phase was removed and treated with a mixture of 1 mL of chloroform, 1 mL of methanol and 0.9 mL KCl/HCl with a ration of 1:1:0.9. The aqueous layer was then counted for total $^3H_2O$ determination. This process resulted in greater than 99.7% extraction and separation of $^3H_2O$ from the palmitate. Average rates of fatty acid oxidation for each phase of perfusion are expressed as nmol/min/g dry wt after taking consideration the dilution factor.

Active compounds are characterized by an increase in glucose oxidation and/or decrease in fatty acid oxidation as compared to the control experiments (DMSO). The compounds that caused statistically significant increases in glucose oxidation and/or decrease in fatty acid oxidation are considered to be active. Statistical significance was calculated using the Student's t test for paired or unpaired samples, as appropriate. The results with $P<0.05$ are considered to be statistically significant.

EXAMPLES

To further illustrate this invention, the following examples are included. The examples should not be construed as specifically limiting the invention. Variations of these examples within the scope of the claims are within the purview of one skilled in the art are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1H$ nuclear magnetic resonance spectra (NMR) is measured in $CDCl_3$ or other solvents as indicated by a Varian NMR spectrometer (Unity Plus 400, 400 MHz for $^1H$) unless otherwise indicated and peak positions are expressed in parts per million (ppm) downfield from tetramethylsilane. The peak shapes are denoted as follows, s, singlet; d, doublet; t, triplet; q, quartet; m, multiplet.

The following abbreviations have the indicated meanings:
Ac=acetyl
Bn=benzyl
Bz=benzoyl
CDI=carbonyl diimidazole
$CH_2Cl_2$=dichloromethane
DIBAL=diisobutylaluminum hydride
DMAP=4-(dimethylamino)-pyridine
DMF=N,N-dimethylformamide
DMSO=dimethylsulfoxide
EDCI or ECAC=1-[3-(dimethylamino)propyl]-3-ethylcarbodiimide hydrochloric acid
ESIMS=electron spray mass spectrometry
$Et_3N$=triethylamine EtOAc=ethyl acetate
HMTA=hexamethylenetetramine
LDA=lithium diisopropylamide
LHDMS=lithium bis(trimethylsilyl)amide
MgSO$_4$=magnesium sulfate
NaH=sodium hydride
NBS=N-bromosuccinimide
NCS=N-chlorosuccinimide
NH$_4$Cl=ammonium chloride
Ph=phenyl
Py=pyridinyl
r.t.=room temperature
TFA=trifluoroacetic acid
THF=tetrahydrofuran
TLC=thin layer chromatography
Tf$_2$O=triflic anhydride
Alkyl Group Abbreviations
Me=methyl
Et=ethyl
n-Pr=normal propyl
i-Pr=isopropyl
n-Bu=normal butyl
i-Bu=isobutyl
t-Bu=tertiary butyl
s-Bu=secondary butyl
c-Hex=cyclohexyl

Example 1

Preparation of 2-cyano-N-isopropyl-N-(2-mercapto-benzothiazol-6-yl)acryl amides

Step 1. Preparation of α-cyano-N-isopropyl-N-(2-mercapto-benzothiazol-6-yl)-acetamide

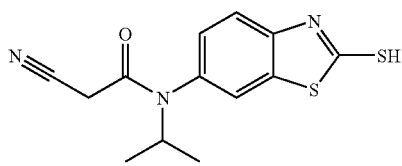

Cyanoacetic acid (1.63 g, 19.17 mmol) was suspended in anhydrous dichloromethane (40 ml). A catalytic amount of N,N-dimethylformamide (0.1 ml) was added and the mixture cooled to 0° C. under an atmosphere of Argon. After 20 minutes stirring at 0° C., oxalyl chloride (1.67 ml, 19.17 mmol) was slowly added to the reaction mixture, which was then allowed to warm to ambient temperature. This mixture was added slowly, after stirring 1 hour, to a 1 M solution of 6-isopropylamino-1,3-benzothiazole-2-thiol (2.16 g, 9.57 mmol) in anhydrous pyridine. After 2 hours the reaction mixture was concentrated in vacuo and partitioned between ethyl acetate and 1 M aqueous citric acid. The resulting precipitate was collected by filtration, combined with the organic extract and concentrated in vacuo. The residue was triturated with diethyl ether to yield 2.32 g (83%). $^1$H NMR (DMSO-d$_6$) δ=0.98 (m, 6H), 3.43 (s, 2H), 4.75 (sep, 1H), 7.27 (d, 1H), 7.35 (d, 1H), 7.63 (s, 1H), 13.94 (s, 1H); ESIMS: m/z 290 (M-H).

Step 2

Preparation of 2-cyano-N-isopropyl-N-(2-mercapto-benzothiazol-6-yl)acryl amides

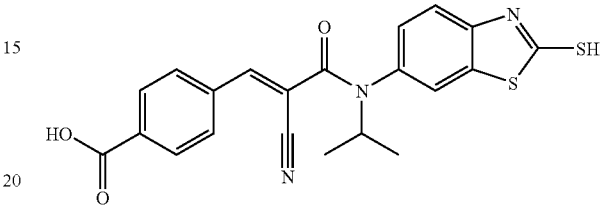

4-{2-Cyano-2-[isopropyl-(2-mercapto-benzothiazol-6-yl)-carbamoyl]-vinyl}-benzoic acid (Table 1, Entry 24)

α-cyano-N-isopropyl-N-(2-mercaptobenzothiazol-6-yl) acetamide (99 mg, 0.339 mmol) and 4-formylbenzoic acid (56 mg, 0.374 mmol) were combined in absolute ethanol (1.4 ml). The mixture was stirred 15 minutes with activated 4 A molecular sieves in a sealed vessel. Piperidine (67 μL, 0.678 mmol) was added and the mixture was heated to 80° C. After 1 hour, the solution was concentrated in vacuo and purified by preparative TLC (10% methanol, 90% dichloromethane) to yield 49 mg (34%). $^1$H NMR (CDCl$_3$) δ1.17 (d, 6H), 4.93 (m, 1H), 7.16 (dd, 1H), 7.28 (dd, 1H), 7.32 (d, 1H), 7.69 (d, 2H), 7.93 (s, 1H), 7.98 (d, 2H); ESIMS: m/z 422 (M-H).

TABLE 1

Preparation of benzothiazole-cyanoacrylamide compounds.

| Examples | R1 |
| --- | --- |
| 1 | 4-(trifluoromethyl)phenyl |
| 2 | 2-methylpropyl |
| 3 | 3-(trifluoromethyl)phenyl |
| 4 | 2-thiopheneyl |
| 5 | 3-thiopheneyl |
| 6 | 4-cyanophenyl |
| 7 | 4-chlorophenyl |
| 8 | 4-butoxyphenyl |
| 9 | cyclohexyl |
| 10 | 3-tetrahydrofuranyl |
| 11 | 2-thiazolyl |
| 12 | 2-(N-methyl)imidazolyl |
| 13 | 4-bromophenyl |
| 14 | 3-chlorophenyl |
| 15 | 3,4-dichlorophenyl |
| 16 | 4-methylphenyl |
| 17 | 4-ethylphenyl |
| 18 | 4-methoxyphenyl |
| 19 | 4-(carboxymethyl)phenyl |
| 20 | 4-(thiomethyl)phenyl |
| 21 | 4-pyridinyl |
| 22 | 3-pyridinyl |
| 23 | 1,4-benzodioxanyl |
| 24 | 4-carboxyphenyl |

Example 2

Preparation of 2-cyano-3-hydroxy-N-isopropyl-N-(2-mercaptobenzothiazol-6-yl)acrylamides

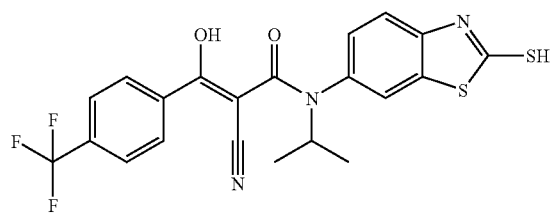

2-Cyano-3-hydroxy-N-isopropyl-N-(2-mercapto-benzothiazol-6-yl)-3-(4-trifluoromethyl-phenyl)-acrylamide (Table 2, Entry 1)

Cooled a 0.1 M solution of α-cyano-N-isopropyl-N-(2-mercaptobenzothiazol-6-yl)acetamide (50 mg, 0.172 mmol) in anhydrous THF to 0° C. Added 60% sodium hydride in mineral oil (69 mg, 1.720 mmol) and stirred 15 minutes. 4-(trifluoromethyl)benzoyl chloride (36 μl, 0.189 mmol) was added dropwise and the mixture stirred an additional 30 minutes. The reaction was quenched by addition of 0.1 M aqueous HCl. The mixture was extracted with ethyl acetate three times, dried over magnesium sulfate and concentrated in vacuo. The residue was purified by preparative TLC (5% methanol, 95% dichloromethane) to yield 27 mg (34%). $^1$H NMR (CDCl$_3$) δ1.17 (d, 6H), 5.01 (m, 1H), 7.12 (d, 1H), 7.21 (dd, 1H), 7.31 (s, 1H), 7.64 (app q, 4H); ESIMS: m/z 462 (M-H).

Example 3

Preparation of 4-{(2-Cyano-2-[isopropyl-(2-mercapto-benzothiazol-6-yl)carbamoyl]vinyl}benzamides

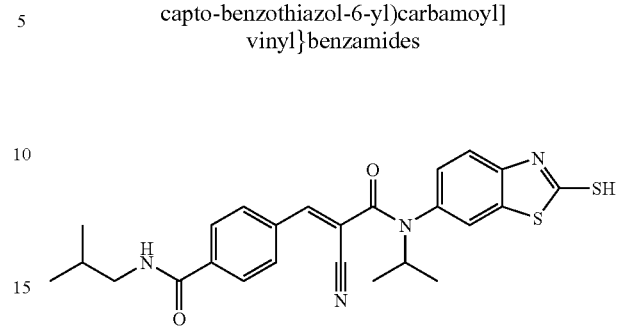

N-isobutyl-4-{2-Cyano-2-[isopropyl-(2-mercapto-benzothiazol-6-yl)carbamoyl]vinyl}-benzamide (Table 3, Entry 1)

Combined 4-{2-Cyano-2-[isopropyl-(2-mercapto-benzothiazol-6-yl)-carbamoyl]-vinyl}benzoic acid (50 mg, 0.118 mmol), isobutylamine (13 μl, 0.130 mmol), HATU (58 mg, 0.153 mmol), and N,N-diisopropylethylamine (27 μl, 0.153 mmol) in anhydrous THF (1.1 ml). The mixture was stirred 2 hours, filtered through celite and concentrated in vacuo. The residue was partitioned between ethyl acetate and 1 M aqueous citric acid. The organic extract was dried over magnesium sulfate and purified by preparative TLC (10% methanol, 90% dichloromethane) to yield 28 mg (50%). $^1$H NMR (CDCl$_3$) δ0.93 (d, 6H), 1.18 (d, 6H), 1.86 (m, 1H), 3.25 (t, 1H), 4.95 (m, 1H), 6.39 (t, 1H), 7.13 (dd, 1H), 7.24 (m, 3H), 7.72 (app q, 4H), 7.91 (s, 1H); ESIMS: m/z 477 (M-H).

TABLE 2 benzothiazole-cyanohydroxyacrylamide compounds.

| Example | R2 |
|---|---|
| 1 | 4-(trifluoromethyl)phenyl |
| 2 | isopentyl |
| 3 | 2,2-dimethylpropyl |
| 4 | benzyl |
| 5 | 2-phenylethyl |
| 6 | 3-(trifluoromethyl)phenyl |
| 7 | 4-cyanophenyl |
| 8 | 4-butoxyphenyl |
| 9 | 2-thiopheneyl |
| 10 | 6-(1-carboxymethyl)hexyl |
| 11 | 6-(1-carboxy)hexyl |

TABLE 3

Amido-benzothiazole-cyanohydroxyacrylamide compounds.

| Examples | R3 |
|---|---|
| 1 | isobutyl |
| 2 | benzyl |
| 3 | 2-methoxyethyl |
| 4 | 2-cyanoethyl |
| 5 | 2,2,2-trifluoroethyl |

Example 4

Step 1. Procedure for the preparation of N-ethyl-4-formylbenzenesulfonamide

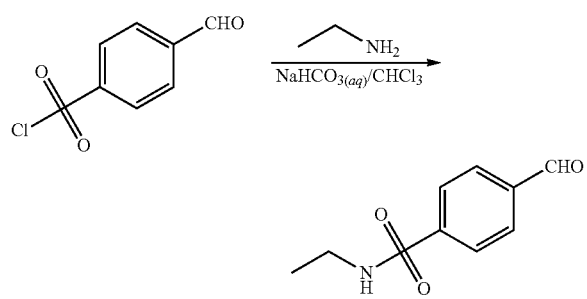

4-formylbenzoyl chloride (50 mg, 0.244 mmol) was dissolved in chloroform (0.5 ml). Saturated aqueous sodium bicarbonate solution (0.5 ml) was added and the two phases were subjected to rapid stirring. A 2 M solution of ethylamine in THF (134 µl) was added and the mixture stirred 1 hour. The organic layer was separated, dried over magnesium sulfate and concentrated in vacuo. The product was used without further purification (52 mg, 100%). $^1$H NMR (CDCl$_3$) δ=1.12 (t, 3H), 3.05 (q, 2H), 4.90 (t, 1H), 8.03 (app d, 4H), 10.09 (s, 1H).

Step 2. Preparation of 2-cyano-3-(4-ethylsulfamoylphenyl)-N-isopropyl-N-(2-mercapto-benzothiazol-6-yl)acrylamide

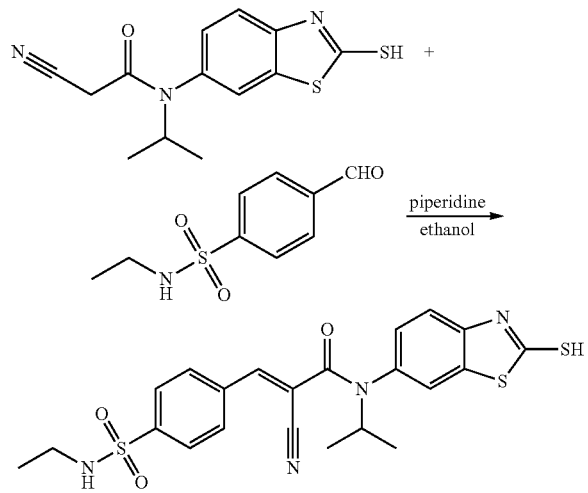

α-cyano-N-isopropyl-N-(2-mercaptobenzothiazol-6-yl)acetamide (71 mg, 0.244 mmol) and N-ethyl-4-formylbenzenesulfonamide (52 mg, 0.244 mmol) were combined in absolute ethanol (1 ml). The mixture was stirred 15 minutes with activated 4 Å molecular sieves in a sealed vessel. Piperidine (27 µL, 0.268 mmol) was added and the mixture was heated to 80° C. After 1.5 hours, the solution was concentrated in vacuo and purified by preparative TLC (50% ethyl acetate, 50% hexanes) to yield 19 mg (16%). $^1$H NMR (CDCl$_3$) δ=1.08 (t, 3H), 1.20 (m, 6H), 2.99 (t, 2H), 4.98 (m, 1H), 5.41 (m, 1H), 7.17 (d, 1H), 7.32 (m, 3H), 7.81 (d, 2H), 7.88 (d, 2H), 7.96 (s, 1H).

TABLE I

In vitro Enzymatic Inhibitory Activities

| Examples | Ki (nM) |
| --- | --- |
| CBM-000302176 | 82.8 |
| CBM-000302199 | 2.0 |
| CBM-000302200 | 109.9 |
| CBM-000302201 | 429.4 |
| CBM-000302202 | 64.9 |
| CBM-000302203 | 167.0 |
| CBM-000302204 | 56.4 |
| CBM-000302205 | 52.8 |
| CBM-000302206 | 336.2 |
| CBM-000302207 | 60.9 |
| CBM-000302208 | 13.2 |
| CBM-000302209 | 11.7 |
| CBM-000302221 | 249.5 |
| CBM-000302222 | 192.5 |
| CBM-000302223 | 8.8 |
| CBM-000302224 | 5.1 |
| CBM-000302225 | 1.9 |
| CBM-000302226 | 1.0 |
| CBM-000302227 | 1.7 |
| CBM-000302228 | 3.2 |
| CBM-000302229 | 10.6 |
| CBM-000302230 | 1.6 |
| CBM-000302231 | 15.4 |
| CBM-000302284 | 28.9 |
| CBM-000302285 | 1.5 |
| CBM-000302286 | 55.8 |
| CBM-000302287 | 31.7 |
| CBM-000302297 | 104.0 |
| CBM-000302298 | 26.2 |
| CBM-000302299 | 2.4 |
| CBM-000302329 | 175.1 |
| CBM-000302371 | 4.1 |
| CBM-000302372 | 4.1 |
| CBM-000302373 | 80.3 |
| CBM-000302427 | 13.3 |
| CBM-000302427 | 13.3 |

TABLE II

Glucose Oxidation of MCD Inhibitors in Isolated Working Rat Hearts

| Examples | MW | GOX (%) |
| --- | --- | --- |
| CBM-000302226 | 413.951 | 113 |
| CBM-000302228 | 385.554 | 167 |
| CBM-000302230 | 386.523 | 272 |

We claim:

1. A compound represented by structural formula (I):

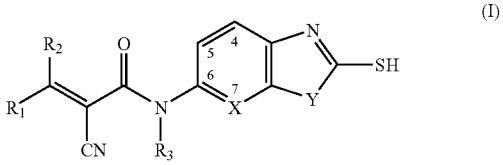

wherein
R$_1$ and R$_2$ are independently hydrogen, hydroxyl, alkoxyl, phenoxyl, substituted phenoxyl, substituted C$_1$-C$_{12}$ alkyl, substituted C$_2$-C$_{12}$ alkenyl, substituted C$_2$-C$_{12}$ alkynyl, phenyl, substituted phenyl, aryl, or heteroaryl, or R$_1$ and R$_2$ together form a 5 to 7 membered ring;
R$_3$ is hydrogen, C$_1$-C$_{12}$ alkyl, substituted C$_1$-C$_{12}$ alkyl, phenyl, substituted phenyl, aryl, or heteroaryl;
X is C or N;

Y is S or O;
its corresponding enantiomers, diastereoisomers or tautomers, or a pharmaceutically acceptable salt, or a prodrug thereof.

2. The compound of claim 1, wherein the compound is represented by structural formulae Ia or Ib:

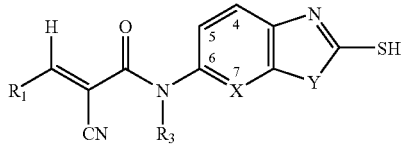

Ia

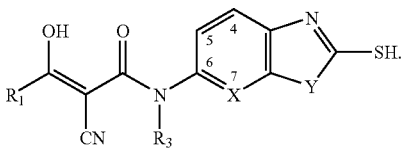

Ib

3. The compound of claim 1 or 2, wherein the compound is represented by structural formulae Ic or Id:

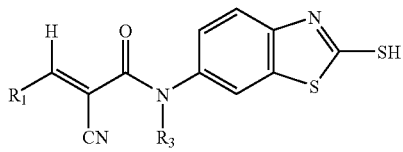

Ic

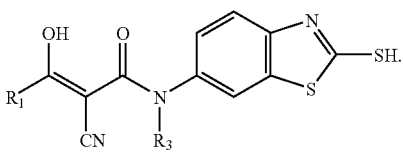

Id

4. The compound of claim 1, wherein the compound is:
2-Cyano-3-hydroxy-N-isopropyl-N-(2-mercapto-benzothiazol-6-yl)-3-(4-trifluoromethyl-phenyl)-acrylamide;
2-Cyano-N-isopropyl-N-(2-mercapto-benzothiazol-6-yl)-3-(4-trifluoromethyl-phenyl)-acrylamide;
2-Cyano-3-hydroxy-4-methyl-hept-2-enoic acid isopropyl-(2-mercapto-benzothiazol-6-yl)-amide;
2-Cyano-3-hydroxy-5,5-dimethyl-hex-2-enoic acid isopropyl-(2-mercapto-benzothiazol-6-yl)-amide;
2-Cyano-3-hydroxy-4-phenyl-but-2-enoic acid isopropyl-(2-mercapto-benzothiazol-6-yl)-amide;
2-Cyano-3-hydroxy-5-phenyl-pent-2-enoic acid isopropyl-(2-mercapto-benzothiazol-6-yl)-amide;
2-Cyano-3-hydroxy-N-isopropyl-N-(2-mercapto-benzothiazol-6-yl)-3-(3-trifluoromethyl-phenyl)-acrylamide;
2-Cyano-3-(4-cyano-phenyl)-3-hydroxy-N-isopropyl-N-(2-mercapto-benzothiazol-6-yl)-acrylamide;
3-(4-Butoxy-phenyl)-2-cyano-3-hydroxy-N-isopropyl-N-(2-mercapto-benzothiazol-6-yl)-acrylamide;
2-Cyano-3-hydroxy-4-thiophen-2-yl-but-2-enoic acid isopropyl-(2-mercapto-benzothiazol-6-yl)-amide;
2-Cyano-5-methyl-hex-2-enoic acid isopropyl-(2-mercapto-benzothiazol-6-yl)-amide;
2-Cyano-N-isopropyl-N-(2-mercapto-benzothiazol-6-yl)-3-(3-trifluoromethyl-phenyl)-acrylamide;
9-Cyano-8-hydroxy-9-[isopropyl-(2-mercapto-benzothiazol-6-yl)-carbamoyl]-non-8-enoic acid methyl ester;
9-Cyano-8-hydroxy-9-[isopropyl-(2-mercapto-benzothiazol-6-yl)-carbamoyl]-non-8-enoic acid;
2-Cyano-N-isopropyl-N-(2-mercapto-benzothiazol-6-yl)-3-thiophen-2-yl-acrylamide;
2-Cyano-N-isopropyl-N-(2-mercapto-benzothiazol-6-yl)-3-thiophen-3-yl-acrylamide;
2-Cyano-3-(4-cyano-phenyl)-N-isopropyl-N-(2-mercapto-benzothiazol-6-yl)-acrylamide;
3-(4-Chloro-phenyl)-2-cyano-N-isopropyl-N-(2-mercapto-benzothiazol-6-yl)-acrylamide;
3-(4-Butoxy-phenyl)-2-cyano-N-isopropyl-N-(2-mercapto-benzothiazol-6-yl)-acrylamide;
2-Cyano-3-cyclohexyl-N-isopropyl-N-(2-mercapto-benzothiazol-6-yl)-acrylamide;
2-Cyano-N-isopropyl-N-(2-mercapto-benzothiazol-6-yl)-3-(tetrahydro-furan-3-yl)-acrylamide;
2-Cyano-N-isopropyl-N-(2-mercapto-benzothiazol-6-yl)-3-thiazol-2-yl-acrylamide;
2-Cyano-N-isopropyl-N-(2-mercapto-benzothiazol-6-yl)-3-(1-methyl-1H-imidazol-2-yl)-acrylamide;
3-(4-Bromo-phenyl)-2-cyano-N-isopropyl-N-(2-mercapto-benzothiazol-6-yl)-acrylamide;
3-(3-Chloro-phenyl)-2-cyano-N-isopropyl-N-(2-mercapto-benzothiazol-6-yl)-acrylamide;
2-Cyano-3-(3,4-dichloro-phenyl)-N-isopropyl-N-(2-mercapto-benzothiazol-6-yl)-acrylamide;
2-Cyano-N-isopropyl-N-(2-mercapto-benzothiazol-6-yl)-3-p-tolyl-acrylamide;
2-Cyano-3-(4-ethyl-phenyl)-N-isopropyl-N-(2-mercapto-benzothiazol-6-yl)-acrylamide;
2-Cyano-N-isopropyl-N-(2-mercapto-benzothiazol-6-yl)-3-(4-methoxy-phenyl)-acrylamide;
4-{2-Cyano-2-[isopropyl-(2-mercapto-benzothiazol-6-yl)-carbamoyl]-vinyl}-benzoic acid methyl ester;
2-Cyano-N-isopropyl-N-(2-mercapto-benzothiazol-6-yl)-3-(4-methylsulfanyl-phenyl)-acrylamide;
2-Cyano-N-isopropyl-N-(2-mercapto-benzothiazol-6-yl)-3-pyridin-4-yl-acrylamide;
2-Cyano-N-isopropyl-N-(2-mercapto-benzothiazol-6-yl)-3-pyridin-3-yl-acrylamide;
2-Cyano-3-(2,3-dihydro-benzo[1,4]dioxin-6-yl)-N-isopropyl-N-(2-mercapto-benzothiazol-6-yl)-acrylamide;
4-{2-Cyano-2-[isopropyl-(2-mercapto-benzothiazol-6-yl)-carbamoyl]-vinyl}-benzoic acid; or
4-{2-Cyano-2-[isopropyl-(2-mercapto-benzothiazol-6-yl)-carbamoyl]-vinyl}-benzoic acid or a pharmaceutically acceptable salt thereof.

* * * * *

UNITED STATES PATENT AND TRADEMARK OFFICE
CERTIFICATE OF CORRECTION

PATENT NO. : 7,897,615 B2  
APPLICATION NO. : 11/866266  
DATED : March 1, 2011  
INVENTOR(S) : Mark D. Kafka Page 1 of 1

It is certified that error appears in the above-identified patent and that said Letters Patent is hereby corrected as shown below:

On the Title Page

Item (73), left hand column (Assignee), line 1, "Sciyaku" should read -- Seiyaku --

Item (57), right hand column (Abstract), line 1, "provides previous methods" should read -- provides methods --

Signed and Sealed this
Thirteenth Day of March, 2012

David J. Kappos
*Director of the United States Patent and Trademark Office*